(12) United States Patent
Van Vilsteren et al.

(10) Patent No.: US 6,290,988 B1
(45) Date of Patent: Sep. 18, 2001

(54) ENCAPSULATED MATERIAL WITH CONTROLLED RELEASE

(75) Inventors: Geertruida Everdina Theodora Van Vilsteren, Doetinchem; Hendrik Jan Neerhof, Wageningen; Eugenius Paulus Henricus Maria Schijvens, Renkum; Didier André Pierre Delnoye, Wageningen; Tjeerd Jongsma, Bennekom, all of (NL)

(73) Assignee: Instituut Voor Agrotechnologisch Onderzoek (ATO-DLO), Wageningen (NL)

( * ) Notice: Subject to any disclaimer, the term of this patent is extended or adjusted under 35 U.S.C. 154(b) by 0 days.

(21) Appl. No.: 09/423,044

(22) PCT Filed: May 1, 1998

(86) PCT No.: PCT/NL98/00241

§ 371 Date: Jan. 6, 2000

§ 102(e) Date: Jan. 6, 2000

(87) PCT Pub. No.: WO98/49910

PCT Pub. Date: Nov. 12, 1998

(30) Foreign Application Priority Data

| May 1, 1997 | (NL) | ................................ 1005948 |
| Dec. 4, 1997 | (NL) | ................................ 1007696 |

(51) Int. Cl.$^7$ ................................ A61K 9/48; A61K 9/42; A61K 9/14
(52) U.S. Cl. ................................ 424/451; 424/463; 424/476; 424/484
(58) Field of Search ................................ 424/451, 463, 424/476; 204/299

(56) References Cited

U.S. PATENT DOCUMENTS

| 4,816,259 | * | 3/1989 | Matthews et al. ............... 424/463 |
| 5,139,794 | | 8/1992 | Patel et al. . |
| 5,164,057 | * | 11/1992 | Mori et al. ............... 204/299 |
| 5,286,502 | | 2/1994 | Meyers . |
| 5,310,558 | * | 5/1994 | Pozzi et al. ............... 424/476 |
| 5,324,445 | | 6/1994 | Langley et al. . |
| 5,484,610 | * | 1/1996 | Bae ............... 424/487 |

FOREIGN PATENT DOCUMENTS

| WO 86/00501 | 1/1986 | (WO) . |
| WO 87/03453 | 6/1987 | (WO) . |
| WO 89/05634 | 6/1989 | (WO) . |
| WO 92/01446 | 2/1992 | (WO) . |

* cited by examiner

Primary Examiner—Thurman K. Page
Assistant Examiner—Blessing Fubara
(74) Attorney, Agent, or Firm—Young & Thompson

(57) ABSTRACT

An encapsulated material is described of which at least a part of the material is kept encapsulated during heat treatment in an aqueous environment and is released during cooling after a heat treatment. The material is encapsulated in a layer of a hydrophobic film-forming material and a layer of a material having a low critical solution temperature (LCST) below the treatment temperature. The layer containing the hydrophobic material may be situated inside the layer having the LCST and have a melting point below the LCST, but it may also be situated outside the layer having the LCST and have a melting point above the LCST of said layer. Said layers may also be applied together.

17 Claims, No Drawings

ENCAPSULATED MATERIAL WITH CONTROLLED RELEASE

FIELD OF THE INVENTION

The invention relates to an encapsulated materiail, in which at least some of the material is released in a controlled manner during cooling aftcr a heat treatment, in particular for use in foodstuffs, cosmetic products, pharmaceuticals, animal feedstuffs, and hygiene products.

BACKGROUND

It is known from *Food Engineering*, 1983, page 59, to coat fortified rice grains with a layer consisting of methylcellulose (MC) and hydroxypropylcellulose (HPMC), with the object of preventing premature extraction of nutrients out of the rice grain during cooking. These cellulose derivatives arc soluble at low temperature (ambient temperature and body temperature) but are not soluble at high temperature. When the rice is introduced into boiling water, the cellulose derivatives ensure that escape of the nutrients is retarded during the cooking of the rice grain and less is therefore thrown away with an excess of cooking water, while the nutrients can still be released later, for example in the body. This reverse solubility behaviour in water, hereinafter referred to as LCST (LCST=lower critical solution temperature), is known for such cellulose derivatives and other polymers.

A disadvantage of this manner of encapsulating foodstuffs and other materials is that, on contact with water or another solvent at low temperature prior to the heat treatment, the materials can escape from the encasing, since the material having the LCST is soluble at low temperature.

It is also known to use polymers with LCST behaviour such as HPMC as a coating material. This polymer has been used widely because it is a food-grade film-forming polymer. HPMC is added to lipid materials in order to produce bilayer films which have a reduced water vapour permeability (see e.g. K; amper et al, *J. Food Sci.*, 1984, 49, 1478–1481; Hagenmaier et al, *J. Agric. Food Chem.*, 1990, 38, 17991803). Commonly two techniques are used to produce bilayer films. The first technique is by casting a lipid layer onto a preformed dry film of HPMC. The second technique is by emulsifying a melted lipid into a solution of HPMC and drying a thin layer of the emulsion. During drying, phase separation will occur, resulting in two different layers: HPMC on the product and the lipid on the outside.

All these systems have similar disadvantages as the method described in *Food Engineering*, 1983, 59. When heating the system, the lipid will melt and be lost in the product, leaving only a cellulosic derivative layer, which shows a release based on Fickian diffusion.

WO 89/05634 describes a sustained-release granular solid medicament form, consisting of a core granule of an excipient material such as lactose, coated with a layer of cellulose ether (HPMC), which is insoluble in hot water. The coating layer contains the active ingredient. The coating liquid, composed of the cellulose ether (5–30% by weight) and the effective ingredient, is applied at a temperature (80° C.) at which the cellulose ether is insoluble. The coated granules can be coated with a further outer layer of a wax-like material, such as paraffins, waxes, higher alcohols, etc. having a melting point between 40 and 90° C. In this method the LCST-behaviour of the cellulose ether is used in the production of the medicaments. A disadvantage of this method is that it is only applicable for heat-stable ingredients.

U.S. Pat. No. 5,310,558 discloses a programmed release oral solid pharmaceutical dosage form comprising a core, containing the active ingredient, optionally subcoated by a film-forming material (HPMC) with polyethylene glycol (PEG), subsequently coated with a layer comprising a mixture of a hydrophobic material (wax), 5–20% of a non-ionic surfactant and 5–30% of a water-soluble film-forming material such as HPMC. The main function of the water-soluble film-fonning material in the hydrophobic layer is to ensure the adhesion of the hydrophobic layer on the core. Heating the described system will result in melting of the hydrophobic layer, resulting in loss of the hydrophobic material of the dosage form. The system may have a further outer enteric coating consisting of methacrylic polymer and triacetin. The system will loose most of the water barrier and the active ingredients will be promptly released into the environment.

SUMMARY OF THE INVENTION

A method has now been found for encapsulating foodstuffs and other materials which does not have these disadvantages. In particular, this novel method of encapsulating is suitable for preparing products which should only release their ingredients after a heat treatment, such as sterilisation or pasteurisation, and a cooling period prior and/or subsequent to the heating treatment. The encapsulated material according to the invention is defined in the accompanying claims.

DETAILED DESCRIPTION OF THE INVENTION

According to the invention, the encapsulated material may first of all be coated with an inner layer of hydrophobic film-forming material which has the function of preventing diffusion of the encapsulated material through the layer having the LCST prior to termination of the heat treatment. This inner hydrophobic layer is primarily of benefit if the encapsulated material is a hydrophilic material. The hydrophobic material for this layer is chosen as a function of the conditions of use. It is preferably a material that is solid or semi-solid at ambient temperature, having a melting point between 30 and 50° C. Suitable materials are fats (semi-hard fats, cocoa butter and the like) and mono- and diglycerides, certain fatty acids such as lauric acid or mixtures of palmitic and stearic acid and the like, lecithins and derivatives and mixtures thereof. Said hydrophobic layer may be applied from the molten state or from a solution or dispersion to the material to be encapsulated, for example from a solution in an alcohol or an ether or from a dispersion in water. The thickness of said layer may be from a few $\mu$m to several mm, or, as a weight ratio, e.g. 10–10,000 ppm with respect to the encapsulated material.

Instead of encapsulating the material with an inner hydrophobic layer, the encapsulated material can also be mixed into said hydrophobic layer, for example as a granulated material or in dissolved form. The function of this material and the requirements imposed thereon are the same as stated above for the hydrophobic material. The mixture must have some non-deformability so that a layer containing LCST material can be applied to it. If the encapsulated material itself is hydrophobic (not soluble in water) the inner hydrophobic layer can be omitted.

Situated around this optional hydrophobic layer is the layer containing the material having low critical solution temperature (LCST). Said LCST material may be a material known for the purpose. Depending on the conditions of use, the LCST is between ambient temperature and the treatment temperature, for example between 30, preferably 40, and 100° C., in particular between 50 and 90° C. The separation or assembly of the polymer on increasing the temperature is a property of any polymer which contains polar or apolar residues in a suitable arrangement. Useful materials having an LCST are, for example, alkylated and/or hydroxvialkylated polysaccharides, such as hydroxypropylmethylcellulose (HPMC), for example Celacol®, ethyl(hydroxyethyl) cellulose (EHEC), hydroxypropylcellulose (HPC), methylcellulose (MC) and mixtures thereof. Mixtures of cellulose ethers with carboxymethylcellulose (CMC) also form suitable LCST polymers. Other polymers which exhibit LCST behaviour in water and which are suitable as coating material are: polymers of mono-or di-N-alkylated acrylamides, copolymers of mono- or di-N-substituted acryl-amides with acrylates and/or acrylic acids or mixtures of interpenetrating networks of the above-mentioned (co-) polymers. Suitable furthermore are polyethylene oxide or copolymers thereof, such as ethylene oxide/propylene oxide copolymers and graft copolymers of alkylated acrylamides with polyethylene oxide. Furthermore: poly-methacrylic acid, polyvinyl alcohol and copolymers thereof, polyvinyl methyl ether, certain proteins, such as poly(VAPGVV), a repeating unit in the natural protein elastin, and certain alginates. Mixtures of said polymers with salts or surfactants can also be used as encapsulating material having an LCST. The LCST temperature can thereby be modified.

The layer containing the LCST may be sprayed from an optionally heated solution or dispersion, for example from a solution in wvater and/or an alcohol. The thickness and mass of said layer having the LCST is comparable with that of the optional first hydrophobic layer. The layer containing the LCST or any other layer may further contain other additives such as colorants, flavorants, fragrances, stabilisers, plasticisers, surfactants, fillers, etc.

The inner hydrophobic layer and the layer having the LCST behaviour may also be applied simultaneously to the material to be encapsulated in the form of a "hybrid" layer by coating or spray-drying with a dispersion or solution of the hydrophobic material and the material having the LCST behaviour. In this connection, care is taken that the hydrophobic material and the material having the LCST behaviour are mixed in the correct ratios in the dispersion or solution so that the desired masses of the two materials are applied to the material to be encapsulated.

To protect the encapsulated material and the layer having the LCST against water or other dissolving media prior to the heat treatment (up to a temperature above the LCST of said layer), the material provided with the layer having the LCST can be further encapsulated with an outer hydrophobic layer. The material of said layer should be solid, or at least not liquid at ambient temperature, and preferably has a melting point or softening point of at least the solution temperature of the layer having the LCST. In particular, the melting point of said layer is between the LCST and the treatment temperature. Suitable materials are semi-solid and solid fats, such as solidified castor oil, crambe oil or other vegetable, animal or semi-synthetic fats, paraffins, beeswax, carnauba wax or other waxes, polymers having a UCST (upper critical solution temperature) which is higher than the LCST of the LCST layer, certain proteins or other materials which are released from the underlying layer at a temperature above the LCST. Said outer hydrophobic layer ensures that the LCST layer does not dissolve when the encapsulated material is introduced into cold water. The outer layer is primarily of importance if the encapsulated material is added to the product to be heated at a temperature below the LCST of the underlying layer.

An important advantage of the invention is the release of ingredients after a heating step. Heating steps are very common in food, feed and non-food industry, for instance pasteurisation or sterilisation. An objective of the heating step is, among other things, to extend the shelf life by killing micro-organisms. The product has to be heated in the closed package (e.g. a jar, bottle, etc), which cannot be opened again to prevent recontamination. Thus, ingredients should nor be added after the heating step. Another method of heating is, for instance, continuous heating and aseptic filling. Aseptic filling is an expensive technique and is very difficult for products with large pieces. Addition of ingredients during the aseptic filling is only possible when the ingredients are sterile. A release of the ingredients after the heating step, without opening the package, offers large advantages.

According to the invention, the ingredient is separated from the product environment by means of a coating or encapsulation system. The trigger for release is the cooling process after the heating treatment. Release after the heating step is important in case of possible negative effects of the ingredient on the product during heating. Mushrooms give higher weight reduction when sterilised in the presence of salt, but the salt is required for taste. Release of the salt after the heat treatment circumvents the disadvantage. Acidity (low pH-values) has a positive effect on quality parameters of the vegetables, such as texture, and the thermal death time of spores to be killed during pasteurisation or sterilisation. The firmness of green beans after sterilisation at neutral pH or at pH =4 and sequential neutralisation gives a firmness of 159 and 230 N, respectively. However, the low pH has a negative effect on the taste. Neutralisation of the acid by release of alkali after the heating step circumvents this disadvantage of the sour taste, but the advantages of acidity during the heat treatment remain. Another important advantage of the invention is the protection of thermally unstable ingredients during the heating step. In the invention the heat unstable ingredient is kept in a dry environment, thus becoming much more stable during heating. As above, the heating step is required and cannot be circumvented in any other way. Addition of the heat unstable ingredients to the packaged product afterwards is not possible. Release of the heat unstable ingredients after heating is very interesting for ingredients with nutritional value, such as vitamins, proteins, peptides, hydrolysates, nutraceuticals, etc., and for functional ingredients, such as colorants, anti-oxidants, thickening agents, preservatives, enzymes, etc.

The encapsulated material according to the invention can be any material which should be released under a certain temperature regime in a target environment. This includes pharmaceuticals, cosmetic products, preservatives, foodstuffs, growth regulators, colorants, flavourings, pesticides and herbicides, and the like, for use in humans and animals, plants, soil, water etc.

The encapsulated ingredients can vary in size from micrometers (e.g. 30 to 1000μm) up to several centimeters, e.g. for tablets. The invention can also be applied for coating larger products, such as nuts, raisins, croutons., breadsticks, and the like.

Moreover, the invention can also be used for applying separating layers or films between distinct parts of a product, e.g. separate parts with different colours, in which migration of ingredients such as colorants should be prevented, or separate parts with different water activity, in which migration of water should be prevented and so on. Such products are referred to herein as semi-solid materials, which means that they are neither thin liquids, nor complete solids, but rather high viscosity, usually aqueous emulsions, pastes, gels, creams or the like. These can be cosmetic products, hygiene products, household products, and especially foodstuffs. two layers should at least be present, a lower hydrophobic layer and an upper LCST layer. A second hydrophobic layer may be present on top of the hydrophobic layer, in order to avoid migration before the heat treatment. To obtain a closed, covering layer, the material to be encapsulated should have a smooth and even surface.

The hydrophobic layers can be applied using procedures such as those known for lipids. A fat can be sprayed onto the material to be encapsulated from a melt or from a solution or dispersion. In this case, the material to be encapsulated is situated on a fluid bed or in a tablet coating pan. The material to be encapsulated may also be dispersed in a molten fat in order then to be processed to form granulated material by spraying. For this purpose, known spray-cooling, spray-freezing or rotating disc procedures can be used. The LCST layer can be applied from an aqueous solvent or another solvent safe for foodstuffs with the aid of spray coating. The material to be encapsulated is contained in this case in a tablet coating pan or on a fluid bed. It is also possible to disperse the material to be encapsulated in the solution with the LCST polymer and then to spray-dry the dispersion. The coating procedures and spray-drying procedures can also be used to apply the hybrid layer by starting from a solution or dispersion of the hydrophobic material and thie material having the LCST behaviour.

Other procedures which can be used to apply a plurality of layers are capillary extrusion procedures. In this case, the material to be encapsulated is dispersed or dissolved in a lipid and passed through a capillary, in which process the encasing layer is coextruded around the core material. Other conventional and convenient coating techniques can be applied as well.

EXAMPLE 1

2.5 g of salt are pressed into a cylindrical tablet. The angles of the tablet are abraded until an oval tablet is produced. The tablet is coated and dried on a fluid bed. The coating is applied by spraying. Two layers are applied. The first layer consists of Emuldan KS60 (5–10 mg) and is applied from an ethanol solution (2.5% Emuldan KS60, 97.5% ethanol). The second layer consists of Celacol (5–10 mg), a hydroxy-propylmethylcellulose having an LCST around 70° C. The Celacol is also applied from an ethanol solution (0.5% Celacol, 7.5% water, 92% ethanol).

The coated tablet is introduced into a beaker containing 200 ml of water at 90–95° C. (time 0). The water is kept at 90–95° C. for 25 minutes, after which cooling is carried out to 20° C. within 15 minutes. From time 0, the conductivity and the temperature are measured and plotted against time. The results are shown in FIG. 1.

From the figure it is evident that, at 92° C. (for 25 minutes) and during cooling (15 minutes), only a small portion of the salt tablet dissolves (approximately 10%). However, at lower temperature (after cooling), the tablet dissolves completely within 20 minutes. An uncoated tablet is dissolved in 200 ml of water at a temperature of 90–95° C. in 4.5 minutes and at a temperature of 20° C. in 20 minutes.

EXAMPLE 2

2.500 g of NaCl were mixed with 7.48 g of the water-soluble and heatresistant colorant Brilliant Blue and finely ground in a mortar. A tablet was pressed from the latter and processed as in Example 1. After applying the inner hydrophobic layer (Emuldan KS60) and the Celacol layer, as specified in Example 1, the outer hydrophobic layer was applied. This layer is composed of partially solidified crambe oil having a melting point of 72° C. which is applied by means of spraying from a heated 2% solution in n-hexane. The powdered coating (2.2 mg) was then heated on both sides of the tablet with the aid of a hot gun until it melted so that a tablet was obtained having a continuous hydrophobic layer.

The coated tablet was introduced into a beaker containing 200 ml of water at 26° C. and stirred for 17 minutes at said temperature. Then the water was heated to 95–99° C. within 13 minutes and kept at said temperature for 15 minutes, after which the whole was cooled to room temperature within 10 minutes. Stirring was continued until the tablet was completely dissolved. During the experiment, samples were taken and their colorant concentration was determined spectrophotometrically. The results of said experiment are shown in FIG. 2.

From said figure it is evident that no release takes place during the stirring at room temperature. After the outer layer has been melted, some release of colorant takes place as a result of diffusion, but this is less than 10%. After cooling, the LCST layer dissolves and the colorant is released into the solution. (The total release of colorant is greater than 100% because the total volume is less than 200 ml as a result of evaporation of water).

EXAMPLE 3

A tablet such as that in Example 2 was coated with a mixture of Celacol (0.5 g) and Emuldan KS60 (0.5 g) in alcohol/water (92.5 g/7 g). 10.9 mg of coating was applied to the tablet by means of spraying.

The tablet was immersed in a beaker containing 200 ml of water at 95–99° C. and heated at said temperature for 16 minutes. Then the water was cooled in 10 minutes to room temperature and stirred at said temperature for 25 minutes. During the experiment, samples were taken and their colorant concentration was determined spectrophotometrically. The results of this experiment are plotted in FIG. 3. A pattern is clearly recognisabic which is very similar to Example 1. This indicates that the inner hydrophobic layer can be applied both prior to and at the same time as the LCST layer.

EXAMPLE 4

2.112 g of NaCl were mixed and ground with 0.405 g of the water-soluble and thermally unstable colorant Beet Red and pressed into a tablet. Said tablet was treated and coated as described in Example 2. The coating layers which were applied to said tablet comprised from thc insidc outwards respectively 7.8 mg, 6.2 mg and 31.4 mg. Said tablet was introduced into 200 ml of water and subjected to the same temperature cycle as described in Example 2. As a control, an identical tablet without coating was subjected to an identical temperature cycle of heating and cooling. The results of this experiment are shown graphically in FIG. 4.

The difference between the two tablets is manifested clearly even at room temperature. The uncoated tablet begins to dissolve and r,eleases the colorant within 14 min, while the coated tablet does not release any colorant. During heating and stirring at 98° C., the colorant released is completely decomposed. The decomposition product has, however, still some absorption at the same wavelength as the starting material, as a result of which it looks as if some starting material is still present after heating. However, from the complete UV-Vis spectrum, it appears that, after completion of the heating step in the case of the uncoated tablet, only decomposition product is present. In the case of the coated tablet, decomposition of colorant also takes place, but only of that material which is dissolved in water as a result of leaks. The bulk of the colorant is released unaffected after cooling.

EXAMPLE 5

A tablet of KCl (2.5 g) and Brilliant Blue (8.8 mg) was treated as in Example 2, with the omission of the inner hydrophobic layer. The tablet was intro-duced into 200 ml of water and heated and cooled as in Example 2. The release profile is shown in FIG. 5.

After the outer hydrophobic layer has melted (approximately 70° C.), an increased release of colorant takes place. After heating for 16 min at more than 90° C., approximately 30% of the colorant has been released. This is significantly more than the colorant release of a pill in which a Celacol+fat layer is applied, as described in Examples 2 and 3. Below the LCST temperature, the Celacol dissolves and the rest of the colorant is released. This example shows that the barrier properties of a polymer having LCST behaviour in water are improved by applying said polymer on top of or together with a hydrophobic layer.

EXAMPLE 6

Salt (NaCl) was combined with mushrooms either directly or using the system of example 2. The weight reduction of the mushrooms after sterilisation in the direct presence of 1.5% NaCl brine and 0.1% citric acid is 34.6%. Release of the salt and acid after the sterilisation process in the same concentration using the invention gave a reduced weight of only 31.6%.

EXAMPLE 7

A tablet as in example 1 is produced and added ti) flasks with 200 ml heated water at 86° C. After 10 minutes at 86° C. the temperature is raised to 120° C. in 16 minutes. After a total of 46 minutes the temperature is iowered to 35° C. (after 182 minutes). The conductivity of the water is measured at diffcrent time intervals during the experiment and the trend is similar to the other examples. Furthermore, the turbidity of the water is determined during the experiment by spectrometry at 780 nm. After sterilisation, the turbidity was approximately 0.01 in comparison to 0.00 for plain water.

EXAMPLE 8

A solution of 250 ml 42.3 mM HCl is heated tc 100° C. A pellet containing 0.423 g NaOH encapsulated in 2 gram salt, is added. The pellet is coated with 8 mg of hybrid coating on a fluidised bed from a solution of 0.5% Celacol, 0.5% Emuldan, 7% $H_{2O}$ and 92% ethanol. Subsequently the solution is sterilised for 15 minutes at 120° C. The pH is indicated using bromo methyl blue, which turns from yellow to blue at pH 7. The base is released after sterilization during cooling. Just at room temperature the solution turns from yellow into blue which indicates the neutralisation of the solution.

EXAMPLE 9

Custard pudding with berry juice is a popular dessert. However, flavours and colorants will migrate from the juice into the custard during storage, which induces the loss of the characteristic colour and flavour of the custard and thereby the loss of quality of the product. A lipid film between the custard and the juice can form a barrier and will therefore improve the product quality. However, during pasteurisation of the product, the lipid film will melt and float to the surface. With the present method it is possible to prevent the creaming of the lipid during pasteurisation.

Custard is bottled in a jar. The surface is coated with a lipid layer (hardened coconut oil, Hardko). Subsequently the lipid layer is covered with a Celacol film from an aqueous solution. After drying the Celacol film, the hot juice is added and the closed jar is pasteurised. After pasteurisation it appears the lipid still forms a layer between the custard and the juice.

What is claimed is:

1. An encapsulated maaterial, the material being encapsulated in at least two layers ensuring that at least a part of the material is kept encapsulated during heat treatment in an aqueous environment and is released after cooling after said heat treatment, said at least two layers comprising a first layer of a hydrophobic film-forming material having a melting point below the temperature of said heat treatment, and a second layer of a material having a low critical solution temperature (LCST below the temperature of said heat treatment, said first hydrophobic layer being situated essentially inside said second layer having the LCST.

2. An encapsulated miaterial according to claim 1, wherein said hydrophobic material has a melting point below the LCST.

3. An encapsulated material according to claim 1, wherein a third layer containing hydrophobic material is situated outside the layer having the LCST.

4. An encapsulated material according to claim 1, wherein the material having the LCST comprises an alkylated and/or hydroxyalkylated polysaccharide.

5. An encapsulated material according to claim 1, wherein the LCST is a temperature between 30 and 100° C.

6. An encapsulated material according to claim 1, wherein the heat treatment temperature is a temperature between 50 and 150° C.

7. An encapsulated material according to claim 1, wherein the temperature of the aqueous environment after and optionally before said heat treatment is between 0 and 50° C.

8. An encapsulated material according to claim 1, wherein the said first hydrophobic layer and said second layer having the LCST have been applied as a mixture.

9. A combination of two adjacent semi-solid materials, wherein at least one material contains an ingredient capable of migrating into the other, the semi-solid materials being separated, in such a manner that migration during heat treatment is prevented, by at least a first layer of a hydrophobic material and a second layer of a material having a low critical solution temperature (LCST) below the temperature of said heat treatment, said second layer having the LCST being situated above said first hydrophobic layer.

10. A combination according to claim 9, wherein a third, hydrophobic layer is situated above said second layer having the LCST.

11. A combination according to claim 9, wherein said semi-solid materials are foodstuffs.

12. A process for adding an active material to a target environment before or during a heat treatment and releasing said material to said target environment after, said heat treatment, by adding said active material in coated form, the material being coated with a layer of a material having a low critcal solution temperature (LCST) below the temperature of said heat treatment and with at least a layer of a hydrophobic film-forming material situated between said active material and said LCST material.

13. A process according to claim 12, wherein said active material is added to said target environment before said heat treatments and said active material is also coated with a hydrophobic layer outside the layer of said LCST material.

14. A process according to claim 12, wherein said active material is coated with a hybrid layer of said hydrophobic material and said LCST material, and an outer layer of hydrophobic material.

15. An encapsulated material according to claim 4, wherein the material having the LCST comprises hydroxipropylrnethylcellulose.

16. An encapsulated material according to claim 6, wherein the heat treatment temperature is a temperature between 60 and 120° C.

17. An encapsulated material according to claim 7, wherein the temperature of the aqueous environment after and optionally before said heat treatment is between 5 and 30° C.

* * * * *